(12) United States Patent
Watanabe et al.

(10) Patent No.: US 8,981,161 B2
(45) Date of Patent: Mar. 17, 2015

(54) PROCESS FOR PRODUCTION OF DITRIMETHYLOLPROPANE

(75) Inventors: Masafumi Watanabe, Okayama (JP); Takeru Nishida, Okayama (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 14/129,471

(22) PCT Filed: Jun. 28, 2012

(86) PCT No.: PCT/JP2012/066553
§ 371 (c)(1),
(2), (4) Date: Dec. 26, 2013

(87) PCT Pub. No.: WO2013/005636
PCT Pub. Date: Jan. 10, 2013

(65) Prior Publication Data
US 2014/0135536 A1 May 15, 2014

(30) Foreign Application Priority Data
Jul. 1, 2011 (JP) .................................. 2011-147558

(51) Int. Cl.
*C07C 41/01* (2006.01)
*C07C 41/06* (2006.01)
*C07C 29/38* (2006.01)
*C07C 45/75* (2006.01)

(52) U.S. Cl.
CPC ................. *C07C 41/06* (2013.01); *C07C 29/38* (2013.01); *C07C 45/75* (2013.01)
USPC ........................................................ 568/680

(58) Field of Classification Search
USPC ........................................................ 568/680
See application file for complete search history.

(56) References Cited

U.S. PATENT DOCUMENTS

| 5,840,994 A | 11/1998 | Ninomiya et al. |
| 2010/0240931 A1 | 9/2010 | Watanabe |

FOREIGN PATENT DOCUMENTS

| JP | 57-139028 | 8/1982 |
| JP | 6-501470 | 2/1994 |
| JP | 8-157401 | 6/1996 |
| JP | 9-268150 | 10/1997 |
| JP | 2005-23067 | 1/2005 |
| WO | WO 2009/057466 A1 | 5/2009 |

OTHER PUBLICATIONS

International Search Report issued Oct. 2, 2012, in PCT/JP12/066553 filed Jun. 28, 2012.

*Primary Examiner* — Sikarl Witherspoon
(74) *Attorney, Agent, or Firm* — Oblon, McClelland, Maier & Neustadt, L.L.P.

(57) ABSTRACT

Provided is a method for producing di-TMP by reacting n-butyl aldehyde (NBD), formaldehyde and a base, said method including a first step of reacting the NBD, formaldehyde (1) and a base (I) to obtain a reaction mixture solution containing trimethylolpropane (TMP), di-TMP and 2-ethyl-2-propenal (ECR); a second step of distilling the reaction mixture solution to recover the ECR therefrom; and a third step of sequentially adding the ECR recovered by distillation, and adding at least one of a base (II) and formaldehyde (2), to the reaction mixture solution from which the ECR has been recovered by distillation, and thereby allowing a reaction for production of the di-TMP to proceed gradually, in which TMP is added in any one of the first to third steps or in plural steps of the first to third steps.

18 Claims, No Drawings

PROCESS FOR PRODUCTION OF DITRIMETHYLOLPROPANE

TECHNICAL FIELD

The present invention relates to a method for producing ditrimethylolpropane (hereinafter referred to as "di-TMP") with a high efficiency.

BACKGROUND ART

In general, di-TMP is obtained as a by-product upon production of trimethylolpropane (hereinafter referred to as "TMP"). Namely, when industrially producing TMP by aldol condensation and crossed Cannizzaro reaction between n-butyl aldehyde (hereinafter referred to as "NBD") and formaldehyde in the presence of a base, di-TMP is produced as a by-product. The solution obtained by the reaction is extracted using a solvent after condensing or without condensing so as to a TMP extract (crude TMP). The crude TMP is purified by distillation under a high vacuum to obtain a TMP product together with a distillation still residue containing from 1 to 20% of TMP and from 20 to 50% of di-TMP. As a method of recovering di-TMP from the distillation still residue, there have been proposed distillation or crystallization using a solvent such as acetate (refer to Patent Document 1), and the like.

In these methods, it is required to separate and recover only di-TMP from a reaction mixture containing raw materials for TMP such as formaldehyde and NBD, a denatured material generated during the recovery of TMP by distillation, or by-products other than di-TMP such as an acetal of TMP and formaldehyde. Also, the content of di-TMP therein is low. Accordingly, it will be difficult to recover di-TMP with a high yield in an industrially efficient manner.

In order to solve these problems, studies have been made to increase an amount of di-TMP by-produced upon production of TMP, and there have been proposed a method of determining the reaction conditions to be specific (refer to Patent Document 2), a method of recovering 2-ethyl-2-propenal (hereinafter referred to as "ECR") that is an intermediate reaction product and adding the same again to the reaction system (refer to Patent Document 3), and the like.

The amount of di-TMP produced in these methods is from about 10 to about 18 mol % based on NBD which is merely as low as from 2 to 4 times an amount of di-TMP by-produced in the conventional methods for producing TMP in which no measure for increasing an amount of di-TMP by-produced has been taken. The amount of di-TMP produced necessarily depends upon an amount of TMP produced because di-TMP is merely a by-product upon production of TMP. Thus, it is not adaptable for the increasing demand for di-TMP.

Also, there has been proposed the method of extracting di-TMP with an organic solvent having no affinity to water by adding the organic solvent to the reaction system (refer to Patent Document 4). However, this method, in which the aimed compound is contained in both of a water layer and an organic layer after the extraction, not only extremely complicates post-treatment after the reaction but also requires distillative recovery of the used organic solvent, and therefore, it is disadvantageous from the industrial viewpoints.

On the other hand, as a method of synthesizing di-TMP itself, there are known a method of producing di-TMP by subjecting two molecules of TMP to dehydrative condensation to produce di-TMP by an ether bond therebetween, a method of synthesizing di-TMP by reacting ECR with TMP and so on. In these methods, the amount of di-TMP produced is not limited by the amount of TMP produced unlike the methods of recovering di-TMP from the distillation still residue.

However, in the method of synthesizing di-TMP by subjecting two molecules of TMP to dehydrative condensation to produce an ether bond therebetween, because of the intermolecular reaction between TMP, the ether condensate that is necessarily generated between three or more molecules of TMP is inevitably by-produced. In order to suppress the by-production, the reaction rate of the dehydrative condensation reaction should be lowered, so that the amount of di-TMP produced is reduced, which is disadvantageous from the industrial viewpoints.

To improve these problems, Patent Document 5 discloses the method in which TMP having three alcoholic hydroxyl groups that are partially previously reacted and formed into a lower fatty acid ester is used as a raw material. However, even in this method, it is not possible to selectively react only two alcoholic hydroxyl groups in a molecule of TMP to form the lower fatty acid ester. Therefore, the method also fails to essentially solve the problem concerning production of the ether condensate of three or more molecules of TMP. In addition, this method further requires an additional step of regenerating di-TMP by hydrolyzing the di-TMP having esterified alcoholic hydroxyl groups which is produced from TMP having one or two esterified alcoholic hydroxyl groups. Thus, the method has increased economical burdens and therefore industrial disadvantages.

Further, in the method of producing di-TMP from ECR and TMP (refer to Patent Document 6), it is required that ECR as the raw material is separately synthesized. Since the yield of ECR from NBD is as low as about 40%, there occurs such a problem that a majority of NBD forms into an unnecessary by-product which should be discarded. Therefore, the method is problematic from the economical viewpoint.

PRIOR ART DOCUMENTS

Patent Documents

Patent Document 1: JP 2005-23067A
Patent Document 2: JP 57-139028A
Patent Document 3: WO 2009/057466A
Patent Document 4: JP 8-157401A
Patent Document 5: JP 6-501470A
Patent Document 6: JP 9-268150A

SUMMARY OF THE INVENTION

Problem to be Solved by the Invention

As described above, in the method of obtaining di-TMP as a by-product of TMP produced by the reaction between NBD and formaldehyde in the presence of a base catalyst, there occurs such a problem that the amount of di-TMP produced is necessarily limited by the amount of TMP produced since the content of di-TMP in the distillation still residue is low and di-TMP is a by-product upon production of TMP.

On the other hand, in the method of directly producing di-TMP as a main product, there occurs such a problem that a majority of NBD used as the raw material forms into an unnecessary by-product which should be discarded, so that the yield of di-TMP is lowered, and large economical burdens tend to be required owing to the complicated process.

In consequence, an object of the present invention is to solve the above problems and provide a method for producing di-TMP in an efficient industrially useful manner.

Means for Solving the Problem

As a result of extensive and intensive researches regarding the methods for producing di-TMP which have suffered from the above-mentioned problems, it has been found that by adding TMP in the course of a process of producing di-TMP, it is possible to produce di-TMP with a high efficiency, and then the present invention has been accomplished. That is, the present invention relates to the method for producing di-TMP as described in the following aspects (A) to (O).

(A) A method for producing di-TMP by reacting NBD, formaldehyde and a base, the method including:
a first step of reacting the NBD, formaldehyde (1) and a base (I) to obtain a reaction mixture solution containing TMP, di-TMP and ECR;
a second step of distilling the reaction mixture solution to recover the ECR therefrom; and
a third step of sequentially adding the ECR recovered by the distillation, and adding at least one of a base (II) and formaldehyde (2), to the reaction mixture solution from which the ECR has been recovered by the distillation, and thereby allowing a reaction for production of the di-TMP to proceed gradually,
TMP being added in any one of the first to third steps or in plural steps of the first to third steps.

(B) The method for producing di-TMP as described in the aspect (A), wherein a total amount of the TMP added is from 0.1 to 5.0 equivalents per 1.0 mol of the NBD.

(C) The method for producing di-TMP as described in the aspect (A) or (B), wherein a total amount of the formaldehyde (1) and the formaldehyde (2) is from 3.0 to 7.0 equivalents per 1.0 mol of the NBD.

(D) The method for producing di-TMP as described in any one of the aspects (A) to (C), wherein a total amount of the base (I) and the base (II) is from 0.8 to 2.5 equivalents per 1.0 mol of the NBD.

(E) The method for producing di-TMP as described in any one of the aspects (A) to (D), wherein an equivalent amount of the base (I) is from 5 to 100% of the total equivalent amount of the base (I) and the base (II).

(F) The method for producing di-TMP as described in any one of the aspects (A) to (E), wherein an equivalent amount of the formaldehyde (1) added in the first step is from 9 to 100% of the total equivalent amount of the formaldehyde (1) and the formaldehyde (2).

(G) The method for producing di-TMP as described in any one of the aspects (A) to (F), wherein a temperature of a reaction in the first step is from 45 to 120° C.

(H) The method for producing di-TMP as described in any one of the aspects (A) to (G), wherein a temperature of the reaction mixture solution in the second step in which the ECR is recovered by the distillation is from 45 to 120° C.

(I) The method for producing di-TMP as described in any one of the aspects (A) to (H), wherein a temperature of a reaction in the third step is from 45 to 120° C.

(J) The method for producing di-TMP as described in any one of the aspects (A) to (I), wherein in the third step, at least one of the formaldehyde (2) and the TMP is added simultaneously with addition of the ECR recovered by the distillation.

(K) The method for producing ditrimethylolpropane as described in the aspect (J), wherein in the third step, the formaldehyde (2) is added simultaneously with addition of the ECR recovered by the distillation, and the addition of the formaldehyde (2) is terminated subsequently to termination of the addition of the ECR.

(L) The method for producing di-TMP as described in any one of the aspects (A) to (K), wherein in the first step, the TMP is added before the reaction between the NBD, the formaldehyde (1) and the base (I).

(M) The method for producing ditrimethylolpropane as described in any one of the aspects (A) to (L), wherein a time required for the addition of the ECR recovered by the distillation is from 10 to 300 min.

Effect of the Invention

According to the present invention, di-TMP can be produced from NBD, formaldehyde, a base and TMP with a high efficiency. In the method of the present invention, upon synthesis of TMP, by adding fresh TMP to the reaction system, an amount of di-TMP by-produced can be increased, thereby enabling production of di-TMP with a high yield. Also, according to the present invention, unreacted raw materials having a boiling point lower than that of di-TMP (such as formaldehyde and TMP) as well as TMP newly produced by the reaction can be recovered by distillation, etc., and recycled. Therefore, NBD is inhibited from forming a non-recyclable by-product which is uselessly discarded. Thus, the present invention provides an extremely excellent industrially useful method.

EMBODIMENTS FOR CARRYING OUT THE INVENTION

According to the present invention, there is provided a method for producing di-TMP by reacting NBD, formaldehyde and a base, the method including:
a first step of reacting the NBD, formaldehyde (1) and a base (I) to obtain a reaction mixture solution containing TMP, di-TMP and ECR;
a second step of recover the ECR therefrom by distillation; and
a third step of sequentially adding the ECR recovered by the distillation, and adding at least one of a base (II) and formaldehyde (2), to the reaction mixture solution, and thereby allowing a reaction for production of the di-TMP to proceed gradually,
TMP being added in any one of the first to third steps or in plural steps of the first to third steps.

In the following, the present invention is described in more detail.

As the NBD used in the present invention, an ordinary commercially available product may be used without any treatment, or a purified product obtained by purifying the commercially available product by distillation, may be used.

The formaldehyde used in the present invention may be in the form of either a formaldehyde aqueous solution or solid paraformaldehyde as long as it is industrially available. The formaldehyde aqueous solution usually contains several percents of methanol as a stabilizer, but such a formaldehyde aqueous solution may be used without any treatment, or may be used in the reaction after subjected to distillation or the like to separate from water or the methanol, if required.

The amounts of the formaldehyde (1) and the formaldehyde (2) are controlled such that a total amount of the formaldehyde (1) and the formaldehyde (2) is preferably from 3.0 to 7.0 equivalents, more preferably from 3.2 to 5.5 equivalents, and still more preferably from 3.5 to 4.5 equivalents per 1.0 mol of the NBD. When the total amount is 3.0 equivalents or more, the di-TMP can be produced with a sufficient yield with a less amount of by-products. When the total amount is 7.0 equivalents or less, a sufficient amount of the di-TMP can be produced on the basis of TMP, and the energy for recovering an excessive amount of TMP is not needed, which is industrially advantageous.

The base (both the base (I) and the base (II)) used in the present invention acts as both a catalyst and a reactant, and either an inorganic base or an organic base may be used. Examples of the organic base include aliphatic amine compounds, in particular, tertiary amines, and the examples thereof include trimethylamine, triethylamine, diethylmethylamine, dimethylethylamine, triisopropylamine, tributylamine, and the like. Examples of the inorganic base include hydroxides of alkali metals or alkali earth metals such as sodium hydroxide, potassium hydroxide, calcium hydroxide and lithium hydroxide; and carbonates of alkali metals or alkali earth metals such as sodium carbonate, potassium carbonate, calcium carbonate and lithium carbonate. Among these, preferred are bases of alkali metals or alkali earth metals, and more preferred are bases containing a carbonate of an alkali metal or a hydroxide of an alkali metal as a main component. From the industrial viewpoints, sodium bases are generally used.

The base (I) and the base (II) may be the same or different from each other. The above-mentioned inorganic bases and organic bases may be used not only singly but also in combination of any two or more thereof, for example, triethylamine as the base (I) may be used in combination with sodium hydroxide as the base (II), or a plurality of the bases may be used in a continuous manner. The base containing a carbonate as a main component may include those carbonates generally commercially available as industrial products or in the form of a mixture with a hydrogen carbonate. Also, for example, in the case where sodium carbonate is used as the base, it is consumed in the reaction to form sodium formate which may be then oxidized into sodium hydrogen carbonate. Such a sodium hydrogen carbonate may be further used as a raw material to produce sodium carbonate; accordingly, the base can be regenerated from the reaction by-product. The bases (I) and (II) may be respectively a mixture of sodium carbonate thus regenerated and sodium hydrogen carbonate.

The total amount of the bases (I) and (II) in the present invention are preferably from 0.8 to 2.5 equivalents, more preferably from 1.0 to 1.5 equivalents, and still more preferably from 1.0 to 1.2 equivalents based on the number of moles of NBD. For example, when using sodium carbonate or calcium hydroxide as a divalent base (2 equivalents), the amount is preferably from 0.8 to 2.5 equivalents (0.4 to 1.25 mol) per 1.0 mol of NBD. When the amount is 0.8 equivalent or more, the raw materials can be prevented from remaining unreacted in a large amount, so that there is no fear that the unreacted raw materials are susceptible to undesirable side reactions. When the amount is 2.5 equivalents or less, the use of a large amount of an acid for neutralization is not needed because the amount of the bases is not excessive.

As TMP used in the present invention, an ordinary commercially available product may be used without any treatment or purified product obtained by purifying the commercially available product by distillation, etc. may be used. In addition, TMP that is produced by this inventive reaction and is purified by distillation or the like can be used by recycling.

The total amount of TMP added in any one of the first to third steps or in plural steps of the first to third steps is preferably from 0.1 to 5.0 equivalents, more preferably from 0.1 to 2.0 equivalents, still more preferably from 0.3 to 1.0 equivalent per 1.0 mol of NBD. When the amount is 0.1 equivalent or more, the raw materials can be inhibited from remaining unreacted in a large amount, so that there is no fear that an amount of by-products from the unreacted raw materials is increased. When the amount is 5.0 equivalents or less, there is no fear that the amount of di-TMP produced based on TMP is reduced.

In the following, the respective steps are described in more detail.

<First Step>

In the reaction method of the present invention, the method of adding the raw materials is not particularly limited. For example, there may be used a method of adding NBD and the base (I) in parallel into an aqueous solution of the formaldehyde (1), a method of first mixing the aqueous solution of the formaldehyde (1) and the base (I), and then adding dropwise NBD into the resulting mixture at a constant rate, or the like. When adding dropwise NBD and the base (I), each of these is preferably added dropwise over a time period of from 1 to 600 min, more preferably from 10 to 360 min, and still more preferably from 10 to 60 min. In case of NBD, NBD may be added dropwise over the same time period as described above. The time of 600 min or shorter is industrially useful in view of a good production efficiency.

The reaction between NBD, the formaldehyde (1) and the base (I) in the first step, in the case where sodium hydroxide is used as the base for example, is represented by the following reaction formula (A).

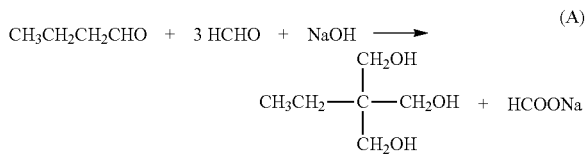

The equivalent amount of the formaldehyde (1) used in the reaction is based on the amount of the formaldehyde to be used that is calculated from the used amount of NBD at a predetermined ratio. The equivalent amount of the formaldehyde (1) added in the first step is preferably from 9 to 100%, more preferably from 58 to 93% and still more preferably from 63 to 88% of the total equivalent amount of the formaldehyde (1) and the formaldehyde (2). When it is 9% or more, the reaction is allowed to proceed sufficiently, so that any side reaction between NBD molecules as the raw material hardly occurs.

The equivalent amount of the base (I) used in the reaction is based on the amount of the base to be used that is calculated from the used amount of NBD at a predetermined ratio. The equivalent amount of the base (I) is preferably from 5 to 100%, more preferably from 20 to 100% and still more preferably from 90 to 100% of the total equivalent amount of the base (I) and the base (II). This ratio for the used amounts may vary depending upon the kind of base. When it is 5% or more, the reaction is allowed to proceed sufficiently, so that any side reaction between NBD molecules as the raw material or the like hardly occurs.

The temperature of the reaction between NBD, the formaldehyde (1) and the base (I) is preferably from 45 to 120° C., and more preferably from 60 to 110° C. When NBD and/or the base (I) are added subsequently, the reaction system may be heated thereafter for 1 to 300 min at a temperature of from 45 to 120° C. to thereby allow the reaction to further proceed. In the case where the temperature of the reaction system is hardly raised to a predetermined temperature owing to reflux of low-boiling substances such as NBD, the formaldehyde and ECR, the reaction system may be pressurized by an inert gas such as a nitrogen gas in order to maintain a predetermined temperature therein. In the case where TMP is added in the first step, the same procedure as described above is conducted.

In the first step, ECR required in the reaction of the third step is produced together with TMP. The reaction for production of ECR is represented by the following reaction formula (B). Also, in the first step, the reaction represented by the reaction formula (C) described hereinlater occurs in simultaneous parallel. Therefore, the reaction mixture solution obtained through the first step contains not only TMP and ECR but also di-TMP. In the present invention, after completion of the first step, the method is transferred to the second step. The second step is preferably initiated after completely consuming a whole amount of NBD, but may be initiated in such a state in which NBD partially remains therein.

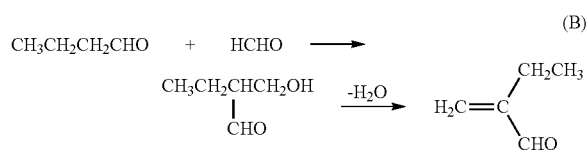

<Second Step: Recovery of ECR by Distillation>

ECR is produced by the dehydration reaction of an alkanal obtained by adding one molecule of formaldehyde to NBD. In the method for producing di-TMP according to the present invention, ECR by-produced during the reaction is separated and recovered out of the reaction system, in parallel with the production reaction of TMP and/or after completion of the production reaction of TMP. The separation and recovery may be easily accomplished by distillation under reduced pressure, under normal pressure or under applied pressure.

ECR is an intermediate product required for production of di-TMP. However, ECR exhibits a high reactivity, and therefore has a such a problem that ECR is consumed owing to side reactions thereof with the other components present in the reaction system. In consequence, if ECR is not recovered by distillation and is thus contained in the reaction mixture solution in a large amount, even when TMP is added from an outside of the reaction system in any step of the first to third steps, it would be difficult to produce di-TMP with a high yield. In addition, since ECR has a boiling point lower than that of water as a solvent, if a large amount of ECR is present in the reaction mixture solution, the reaction temperature tends to be hardly raised, so that the production reaction of di-TMP is inhibited from proceeding. Therefore, in the present invention, it is necessary that ECR is once removed from the reaction solution in the second step.

In order to further suppress production of by-products derived from ECR, it is preferred that a whole amount of ECR is separated and recovered. However, actually, the separation and recovery of ECR may be terminated at the time at which the change in temperature of a distillate upon the recovery of ECR by distillation is stabilized and a substantial amount of ECR is recovered by distillation. This is because the problem of by-production of colored components which will occur owing to a large heat history when the recovery of ECR is preferentially conducted should be avoided.

The amount of ECR recovered by the distillation is preferably in the range of from 0.05 to 0.9 equivalent, and more preferably from 0.1 to 0.7 equivalent per 1.0 mol of NBD as the raw material. When it falls within the above-specified range, a sufficient amount of the aimed di-TMP can be produced in an industrially advantageous manner.

In the recover of ECR by distillation, since ECR undergoes azeotropy with water, the distillate produced in the distillation contains a certain amount of water, and the distillate may be immediately separated into an oil layer and a water layer. However, if the amount of water distilled off is small, etc., the distillate may not be separated into these two layers. The amount of water distilled is preferably from 0.01 to 20 times, more preferably from 0.1 to 8.0 times and still more preferably from 0.1 to 2.0 times a mass of ECR distilled. When the amount is 0.01 time or more, methanol which is extracted in the water layer side is prevented from remaining in the oil layer side, so that there is no fear that the methanol is reacted with ECR to produce a by-product. On the other hand, when the amount is 20 times or less, the time for the distillation step is not prolonged, which is therefore industrially advantageous.

Although the produced distillate contains not only ECR, but also water and organic components such as methanol, the distillate may be added to the reaction solution in the reaction of the third step without any treatment, or the distillate may be subjected to purification treatment such as distillation and then added thereto. When the distillate is separated into two layers, an oil layer and a water layer may be added to the reaction solution while it is still separated or may be added thereto in the form of an emulsion after stirring and mixing, or the respective layers after isolated from each other may be individually added thereto. Further, the method in which after adding one of the oil layer and the water layer, the remaining one layer may be then added or the like can be adopted.

The temperature of the reaction mixture solution during the distillation in the second step for recovering ECR by distillation is preferably from 45 to 120° C.

Also, after recovering ECR by distillation, in the reaction system, a large amount of TMP is newly produced but in a part of the production there may be intermediate products due to the reaction proceeding in the course of the reaction. Accordingly, in order to convert the intermediate products into TMP, the reaction mixture solution obtained after the recovery by distillation may be heated at a temperature of from 45 to 120° C. for a time period of from 1 to 300 min to complete the reaction. When adding the fresh TMP in the second step, the same procedure as described above is conducted.

<Third Step>

Thereafter, ECR recovered by distillation is sequentially added to the reaction mixture solution containing TMP after recovering ECR therefrom in the second step, and at least one of the base (II) and the formaldehyde (2) is added to the reaction mixture solution and thereby the reaction represented by the below-mentioned reaction formula (C) is allowed to proceed gradually. The amount of the formaldehyde (2) to be added is based on the amount of the formaldehyde to be used that is calculated from the used amount of NBD at a predetermined ratio, and the remaining formaldehyde not added in the first step among the whole is used. Similarly, the equivalent amount of the base (II) is based on the amount of the base to be used that is calculated from the used amount of NBD at the predetermined ratio, and the remaining base not added in the first step among the whole is used. ECR recovered by distillation and at least one of the base (II) and the formaldehyde (2) may be sequentially added by in-order addition of the respective components, simultaneous in-parallel addition of the components, or the like, and subjected to the reaction in the third step. Among these methods, preferred is simultaneous in-parallel addition. In the simultaneous in-parallel addition, the addition of any of the components may be first terminated.

The sequential addition as used herein means not the manner of adding the raw materials to the reaction system all at once, but the manner of adding the raw materials to the reaction system over a predetermined time period while allowing the reaction between the raw materials charged thereto to proceed. The sequential addition may be conducted by non-continuous intermittent addition of the raw materials, and is preferably conducted by continuous addition of the raw materials.

The time required for the sequential addition of ECR is preferably from 10 to 300 min, more preferably from 10 to 200 min, still more preferably from 10 to 100 min, and further still more preferably from 10 to 50 min. Thus, when ECR is added for such a prolonged period of time, the production of by-products derived from ECR is prevented, so that the production reaction of di-TMP can be enhanced in selectivity thereof.

The time required for the sequential addition of the formaldehyde (2) is for example in the range of from 1 to 300 min, and is preferably longer than the time required for the addition of ECR, more preferably from 30 to 200 min, and still more preferably from 40 to 90 min. With the time of the addition of the formaldehyde being prolonged, for example, in the case where ECR and the formaldehyde (2) are added by the simultaneous in-parallel addition, the addition of ECR is first terminated, and then the addition of the formaldehyde (2) is terminated.

Thus, when the time of the addition of the formaldehyde (2) is prolonged or when the addition of ECR is first terminated, the formaldehyde is sequentially consumed in the production reaction of di-TMP represented by the below-mentioned formula (C), so that the amount of the formaldehyde in the reaction system is prevented from being excessive. Thus, by decreasing the amount of the formaldehyde in the reaction system, it is possible to suppress the production of by-products which are hardly separated and purified.

If adding the base (II) in the third step, the time required for the sequential addition of the base (II) is preferably from 1 to 300 min, more preferably from 1 to 200 min, and still more preferably from 1 to 100 min. Further, in the third step, both the base (II) and the formaldehyde (2) are preferably added from the viewpoints of enhancing a yield of the reaction product and suppressing the production of by-products.

In the present invention, for example, when using sodium hydroxide as the base, the reaction between TMP, ECR recovered by distillation, the formaldehyde (1) or (2) and the base (I) or (II) in the third step is represented by the following reaction formula (C).

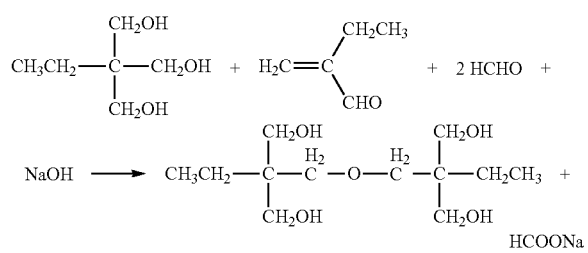

(C)

When the reaction represented by the reaction formula (C) is allowed to proceed while adding ECR recovered by distillation and at least one of the formaldehyde (2) or the base (II), the reaction temperature of the reaction mixture solution may vary depending upon the kind of base used, and is preferably from 45 to 120° C., and more preferably from 60 to 120° C. In particular, when using a carbonate as the base, it is necessary that the temperature is maintained to allow a reaction of converting the hydrogen carbonate produced in the above reaction into a carbonate to proceed sufficiently, and therefore, the reaction temperature is preferably from 60 to 120° C., and more preferably from 80 to 120° C. In this reaction, in order to suppress reflux of low-boiling substances and maintain a predetermined reaction temperature in the reaction system, the system may be pressurized by an inert gas such as a nitrogen gas. When adding the fresh TMP in the third step, the same procedure as described above is conducted.

In the case where ECR as the raw material is not completely consumed at the time at which the addition of all of the raw materials to be added in the third step (i.e., ECR recovered by distillation, and the base (II) and/or the formaldehyde (2)) is terminated, the reaction is completed by further heating. The reaction temperature in such a case may also vary depending upon the kind of base used, and is preferably from 45 to 120° C., and more preferably from 60 to 120° C. In particular, when using a carbonate as the base (II), it is necessary that the temperature is maintained to allow a reaction of converting the hydrogen carbonate produced in the above reaction into a carbonate to proceed sufficiently, and therefore, the reaction temperature is preferably from 60 to 120° C., and more preferably from 80 to 120° C. In this reaction, in order to suppress reflux of low-boiling substances and maintain a predetermined reaction temperature in the reaction system, the system may be pressurized by an inert gas such as a nitrogen gas. When adding the fresh TMP in the third step, the same procedure as described above is conducted.

In addition, it is preferred that the temperature of the reaction in the third step is higher than the temperature of the reaction in the first step, so that the production reaction of di-TMP can be further accelerated. Since the low-boiling ECR is recovered by distillation in the second step to reduce the amount of ECR in the reaction system, the temperature of the reaction in the third step can be easily made to be a relatively high temperature.

The time required for completing the reaction by heating after terminating the addition of ECR recovered by distillation and the base (II) and/or the formaldehyde (2) is preferably from 1 to 180 min, and more preferably from 30 to 120 min. When the time is 180 min or shorter, the reaction solution is prevented from suffering from coloration. When adding the fresh TMP in the third step, the same procedure as described above is conducted.

<Addition of TMP>

The added amount of TMP in any one of the first to third steps or in plural steps of the first to third steps is based on the amount of TMP to be used that is calculated from the used amount of NBD at a predetermined ratio. In the present invention, it is preferred that TMP is added to the reaction system at least one of the first step and the third step. The amount of TMP added in the first step or the third step is preferably from 20 to 100% and more preferably from 50 to 100% of the total amount of TMP to be added. In the present invention, it is more preferred that TMP is added in the first step.

The addition method of TMP to be added in any one of the first to third steps or in plural steps of the first to third steps is not particularly limited.

When adding TMP in the first step, it is preferred that TMP is added before the reaction between NBD, the formaldehyde (1) and the base (I), i.e., before charging at least one of these three raw materials into the reaction system. For example, in the case where NBD and the base (I) are added in parallel into the aqueous solution of the formaldehyde (1) in the first step, it is preferred that TMP is previously added to the aqueous solution of the formaldehyde (1) before adding NBD and the base (I) thereto. On the other hand, in the case where NBD is added to a mixture of the aqueous solution of the formaldehyde (1) and the base (1), it is preferred that TMP is also added to the mixture before adding NBD thereto.

Further, when adding TMP in the third step, it is preferred that the addition of TMP is terminated earlier than termination of the addition of ECR. For example, there may be used such a method in which TMP and ECR are simultaneously added in parallel and the addition of TMP is terminated before the termination of the addition of ECR. In this method, in the case where the formaldehyde (2) is added in the third step, the formaldehyde (2) may also be added in simultaneous parallel with the addition of TMP and ECR, and the addition of the formaldehyde (2) is preferably terminated subsequently to termination of the addition of ECR.

Also, when adding TMP in the second step, it is preferred that TMP is added to the reaction solution that is present in a bottom of a distillation column at a late stage of distilling-off of ECR for a time period as short as possible. As a result, it is possible to increase the amount of TMP in the reaction solution for the initiation of the third step.

It is preferred that TMP is added in the first step or the third step.

The configuration of TMP added is not particularly limited. For example, there may be used a method of adding TMP dissolved in a solvent such as water and methanol, a method of adding a melt of TMP, or a method of adding solid TMP. When adding TMP in the first step and/or the third step, TMP may be dissolved in the reaction raw materials other than TMP which are to be added in the step, such as formaldehyde and may be then added.

The addition time of TMP is also not particularly limited. For example, there may be used a method of adding TMP at one time upon initiation of the respective steps; or a method of continuously adding TMP in which the TMP and the other reaction raw materials to be added in the respective steps are added in the predetermined order, or in which the TMP is simultaneously added together with the other reaction raw materials in parallel in the case where TMP is added in the first step and/or the third step. The time required for the continuous addition is preferably from 1 to 200 min, more preferably from 1 to 100 min, and still more preferably from 1 to 50 min.

The temperature upon the addition of TMP may be such a temperature capable of providing optimum conditions in each of the first to third steps, and is preferably from 45 to 120° C. In the case where TMP is added in the third step and a carbonate is used as the base (II), the temperature is preferably from 60 to 120° C.

<Isolation of di-TMP>

In order to isolate and purify the aimed di-TMP from the resulting reaction solution, TMP is first separated and purified from the reaction solution according to an ordinary TMP purification procedure, and then di-TMP is recovered and purified from the obtained residue by an ordinary method. The method is not particularly limited. For example, there may be used such a method in which after neutralizing the reaction solution, the formaldehyde as the raw material is recovered by distillation and an extraction is conducted, and then di-TMP is recovered and purified by distillation and/or crystallization.

In the present invention, the reactions in the first step and the third step may be respectively carried out in separate reactors under the same or different conditions, or may be sequentially carried out in the same single reactor without separating. For example, the reaction in the first step may be carried out using triethylamine as the base (I), and then the reaction in the third step may be carried out using sodium hydroxide as the base (II). Also, all of the reactions and procedures including the first to third steps as well as isolation of TMP may be carried out in separate exclusive devices for each reaction or procedure, or may be carried out in one or plural devices capable of adapting to the reactions or procedures.

In addition, in the production method of the present invention, TMP and di-TMP are produced via the first to third steps. For this reason, in the case where the procedures of the first to third steps are repeated in this order to continuously produce TMP and di-TMP, the TMP contained in the reaction mixture solution obtained via the first to third steps may be separated from the reaction mixture solution, and then recycled; namely added to the reaction system of any of the first to third steps, which is enable to repeatedly conduct production of di-TMP with little need of additional TMP. In addition, since TMP is industrially usable as a raw material for various materials, TMP not recycled may also be effectively utilized.

EXAMPLES

The present invention will be described in more detail below by referring to the following examples. It should be noted, however, that the following examples are not intended to limit the invention thereto.

The raw materials used in the following Examples were commercially available reagents and the like. More specifically, products commercially available from Mitsubishi Gas Chemical Co., Inc. were used as an aqueous formaldehyde solution and TMP, a product commercially available from Mitsubishi Chemical Corp. was used as NBD, and guaranteed reagents commercially available from Wako Pure Chemical Industries, Ltd were used as sodium carbonate and sodium hydroxide. Further the analysis was conducted using gas chromatography (GC) with diluting a reaction solution and an internal standard sample (neopentyl glycol) with an acetone solvent.

[Analysis Conditions of GC]

Apparatus: "HP-5890" (available from Agilent Technologies Corp.)

Column used: "DB-1" (available from Agilent Technologies Corp.)

Analyzing Conditions: Injection temperature: 250° C.

Detector temperature: 250° C.

Column Temperature Held at 60° C. for 6 min→raised to 250° C. at a rate of 7° C./min→Held at 250° C. for 20 min Detector: Flame ionization detector (FID)

Example 1

Addition of 0.81 Mol of TMP in First Step; Split Addition of Formaldehyde; Split Addition of Base First Step: A 5 L titanium pressure reaction vessel equipped with a temperature controller, a heater, a nitrogen inlet tube and a reflux condenser was charged with 495 g of a 30% by mass formaldehyde (1) aqueous solution (4.9 mol as formaldehyde; 2.6 equivalents based on NBD; 72% of total used amount of formaldehyde) and 108 g of TMP (0.81 mol; 0.43 equivalent based on NBD), followed by heating the contents of the reaction vessel to 70° C. Thereafter, while gradually heating the contents of the reaction vessel, 135 g (1.9 mol) of NBD and 475 g of a 20% by mass sodium carbonate aqueous solution (1.8 mol as base; 0.95 equivalent based on NBD; 94% of total used amount of base) were added thereto using two feed pumps over 30 min, and the resultant was further heated at 77° C. for 3 min.

Second Step: After heating, ECR was recovered by distillation at 100° C. for 30 min. The distillate recovered by distillation contained 16.8 g of an oil layer (corresponding to 0.20 mol of ECR; 0.11 equivalent based on NBD) and 0 g of a water layer.

Third Step: The simultaneous dropwise addition of the resulting distillate and 140 g of a 40% by mass formaldehyde (2) aqueous solution (1.9 mol as formaldehyde; 0.99 equivalent based on NBD; 28% of the total used amount of formaldehyde) into the reaction vessel was initiated using two feed pumps, and both were added dropwise to the reaction mixture solution for 19 min and 68 min, respectively, while maintaining the temperature of the reaction mixture solution at 100° C. After completion of the dropwise addition, the resultant was held under heating at 100° C. for 30 min, and then 22.6 g of a 20% by mass sodium hydroxide aqueous solution (0.11 mol as base; 0.06 equivalent based on NBD; 6% of total used amount of base) were added dropwise thereto using a feed pump over 12 min. After completion of the dropwise addition, the resultant was further held under heating at 100° C. for 39 min.

As a result of analyzing the resulting reaction mixture solution by GC, it was confirmed that the amounts of TMP and di-TMP as calculated values were 253 g and 66.0 g, respectively, and the yields were 57.5% and 28.1%, respectively, on the basis of NBD as the raw material and the total yield of TMP and di-TMP was 85.6%. The amount of TMP newly produced by the reaction corresponds to 134% of an amount of TMP required in the subsequent reaction when it was recycled as the raw material in the subsequent reaction. The results are shown in Tables 1 and 2.

Example 2

Addition of 0.81 Mol of TMP in Third Step; Split Addition of Formaldehyde; Split Addition of Base First Step: A 5 L titanium pressure reaction vessel equipped with a temperature controller, a heater, a nitrogen inlet tube and a reflux condenser was charged with 445 g of a 33% by mass formaldehyde (1) aqueous solution (4.9 mol as formaldehyde; 2.6 equivalents based on NBD; 72% of the total used amount of formaldehyde), followed by heating the contents of the reaction vessel to 70° C. Thereafter, while gradually heating the contents of the reaction vessel, 135 g (1.9 mol) of NBD and 475 g of a 20% by mass sodium carbonate aqueous solution (1.8 mol as base; 0.95 equivalent based on NBD; 94% of the total used amount of base) were added to the reaction vessel using two feed pumps over 30 min, and the resultant was further heated at 80° C. for 3 min.

Second Step After heating, ECR was recovered by distillation at 100° C. for 30 min. The distillate recovered by distillation contained 33.4 g of an oil layer (corresponding to 0.40 mol of ECR; 0.21 equivalent based on NBD) and 2.0 g of a water layer (corresponding to 0.06 time by mass based on the oil layer).

Third Step The simultaneous dropwise addition of the resulting distillate, 140 g of a 40% by mass formaldehyde (2) aqueous solution (1.9 mol as formaldehyde; 0.99 equivalent based on NBD; 28% of the total used amount of formaldehyde) and 158 g of a 68% by mass TMP aqueous solution (0.81 mol as TMP; 0.43 equivalent based on NBD) into the reaction vessel was initiated using three feed pumps, and the three components were added dropwise to the reaction mixture solution for 29 min, 73 min and 12 min, respectively, while maintaining the temperature of the reaction mixture solution at 100° C. Meanwhile, the distillate already separated into two layers was added in the order of the water layer and the oil layer. After completion of the dropwise addition, the resultant was held under heating at 100° C. for 30 min, and then 22.6 g of a 20% by mass sodium hydroxide aqueous solution (0.11 mol as base; 0.06 equivalent based on NBD; 6% of the total used amount of base) was added dropwise thereto using a feed pump over 12 min. After completion of the dropwise addition, the resultant was further held under heating at 100° C. for 39 min.

As a result of analyzing the resulting reaction mixture solution by GC, it was confirmed that the amounts of TMP and di-TMP produced as calculated values were 257 g and 58.5 g, respectively, and the yields were 59.0% and 24.9%, respectively, and the total yield of TMP and di-TMP was 83.9% on the basis of NBD as the raw material. The amount of TMP newly produced by the reaction corresponds to 111% of an amount of TMP required in the subsequent reaction when it was recycled as the raw material in the subsequent reaction. The results are shown in Tables 1 and 2.

Example 3

Addition of 1.0 Mol of TMP in Third Step; Split Addition of Formaldehyde; Split Addition of Base First Step: A 5 L titanium pressure reaction vessel equipped with a temperature controller, a heater, a nitrogen inlet tube and a reflux condenser was charged with 475 g of a 33% by mass formaldehyde (1) aqueous solution (5.3 mol as formaldehyde; 2.8 equivalents based on NBD; 78% of the total used amount of formaldehyde), followed by heating the contents of the reaction vessel to 70° C. Thereafter, while gradually heating the contents of the reaction vessel, 135 g (1.9 mol) of NBD and 475 g of a 20% by mass sodium carbonate aqueous solution (1.8 mol as base; 0.95 equivalent based on NBD; 94% of the total used amount of base) were added to the reaction vessel using two feed pumps over 30 min, and the resultant was further heated at 80° C. for 3 min.

Second Step: After heating, ECR was recovered by distillation at 100° C. for 30 min. The distillate recovered by distillation contained 23.6 g of an oil layer (corresponding to 0.28 mol of ECR; 0.15 equivalent based on NBD) and 1.0 g of a water layer (corresponding to 0.04 time by mass based on the oil layer).

Third Step: The simultaneous dropwise addition of the resulting distillate, 112 g of a 40% by mass formaldehyde (2) aqueous solution (1.5 mol as formaldehyde; 0.79 equivalent based on NBD; 22% of the total used amount of formaldehyde) and 186 g of a 73% by mass TMP aqueous solution (1.0 mol as TMP; 0.54 equivalent based on NBD) into the reaction vessel was initiated using three feed pumps, and the three components were added dropwise to the reaction mixture solution for 24 min, 60 min and 21 min, respectively, while maintaining the temperature of the reaction mixture solution at 100° C. Meanwhile, the distillate already separated into two layers was added in the order of the water layer and the oil layer. After completion of the dropwise addition, the resultant was held under heating at 100° C. for 30 min, and then 22.6 g of a 20% by mass sodium hydroxide aqueous solution (0.11 mol as base; 0.06 equivalent based on NBD; 6% of total used amount of base) were added dropwise thereto using a feed pump over 11 min. After completion of the dropwise addition, the resulting reaction mixture solution was further held under heating at 100° C. for 39 min.

As a result of analyzing the resulting reaction mixture solution by GC, it was confirmed that the amounts of TMP and di-TMP produced as calculated values were 301 g and 51.8 g, respectively, and the yields were 65.5% and 22.0%, respectively, and the total yield of TMP and di-TMP was 87.5% on the basis of NBD as the raw material. The amount of TMP newly produced by the reaction corresponds to 101% of an amount of TMP required in the subsequent reaction when it was recycled as the raw material for the subsequent reaction. The results are shown in Tables 1 and 2.

Comparative Example 1

No Addition of TMP; Split Addition of Formaldehyde; Split Addition of Base

First Step: A 5 L titanium pressure reaction vessel equipped with a temperature controller, a heater, a nitrogen inlet tube and a reflux condenser was charged with 495 g of a 30% by mass formaldehyde (1) aqueous solution (4.9 mol as formaldehyde; 2.6 equivalents based on NBD; 72% of the total used amount of formaldehyde), followed by heating the contents of the reaction vessel to 69° C. Thereafter, while gradually heating the contents of the reaction vessel, 135 g (1.9 mol) of NBD and 475 g of a 20% by mass sodium carbonate aqueous solution (1.8 mol as base; 0.95 equivalent based on NBD; 92% of the total used amount of base) were added to the reaction vessel using two feed pumps over 30 min, and the resultant was further heated at 80° C. for 3 min.

Second Step After heating, ECR was recovered by distillation at 100° C. for 30 min. The distillate recovered by distillation contained 24.7 g of an oil layer (corresponding to 0.29 mol of ECR; 0.16 equivalent based on NBD) and 4.0 g of a water layer (corresponding to 0.16 time by mass based on the oil layer).

Third Step The simultaneous dropwise addition of the resulting distillate and 140 g of a 40% by mass formaldehyde (2) aqueous solution (1.9 mol as formaldehyde; 0.99 equivalent based on NBD; 28% of the total used amount of formaldehyde) into the reaction vessel was initiated using two feed pumps, and the both components were added dropwise to the reaction mixture solution for 36 min and 62 min, respectively, while maintaining the temperature of the reaction mixture solution at 100° C. After completion of the dropwise addition, the resultant was held under heating at 100° C. for 30 min, and then 30.5 g of a 20% by mass sodium hydroxide aqueous solution (0.15 mol as base; 0.08 equivalent based on NBD; 8% of the total used amount of base) was added dropwise thereto using a feed pump over 15 min. After completion of the dropwise addition, the resultant was further held under heating at 100° C. for 36 min.

As a result of analyzing the resulting reaction mixture solution by GC, it was confirmed that the amounts of TMP and di-TMP produced as calculated values were 165 g and 42.6 g, respectively, and the yields were 65.6% and 18.1%, respectively, and the total yield of TMP and di-TMP was 83.7% on the basis of NBD as the raw material. The results are shown in Table 1.

TABLE 1

| Raw materials | | Example 1 | Example 2 | Example 3 | Comparative Example 1 |
|---|---|---|---|---|---|
| NBD (mol) | | 1.9 | 1.9 | 1.9 | 1.9 |
| Equivalent amount of formaldehyde | (1) | 2.6 | 2.6 | 2.8 | 2.6 |
| | (2) | 0.99 | 0.99 | 0.79 | 0.99 |
| per 1 mol of NBD | Total | 3.59 | 3.59 | 3.59 | 3.59 |
| | (1)/total (%) | 72% | 72% | 78% | 72% |
| Equivalent amount of base per 1 mol of NBD | (I) | 0.95 | 0.95 | 0.95 | 0.95 |
| | (II) | 0.06 | 0.06 | 0.06 | 0.08 |
| | Total | 1.01 | 1.01 | 1.01 | 1.03 |
| | (I)/total (%) | 94% | 94% | 94% | 92% |
| Equivalent amount of TMP per 1 mol of NBD | | 0.43 | 0.43 | 0.53 | — |
| TMP adding step | | First step | Third step | Third step | — |
| Yield based on NBD (%) | TMP | 57.5 | 59.0 | 65.5 | 65.6 |
| | di-TMP | 28.1 | 24.9 | 22.0 | 18.1 |
| | TMP + di-TMP | 85.6 | 83.9 | 87.5 | 83.7 |

Comparative Example 2

Separate Synthesis of ECR, Direct Synthesis of di-TMP by Reaction Between ECR and TMP Synthesis of ECR: A 500 mL glass flask equipped with a stirrer was charged with 117 g (1.6 mol) of NBD, and while maintaining an inside temperature of the flask at 30° C., 122 g of a 40% formaldehyde aqueous solution (1.6 mol as formaldehyde) were added dropwise into the flask over 20 min. After 5 min from initiation of the dropwise addition of the formaldehyde, a 20% by mass sodium carbonate aqueous solution in an amount corresponding to 8.5 g of sodium carbonate (0.16 mol as base) was added dropwise into the flask over 20 min using a pump. Thereafter, the resultant mixture solution was subjected to total reflux over 120 min by heating. Then, distillation was conducted under normal pressures, thereby obtaining a fraction distilled off until reaching a distillation column top temperature of 100° C. which was separated into 76 g of an organic phase and 23 g of a water phase. As a result of GC, 58.0 g of ECR were in the organic phase, whereas 15.0 g of TMP were produced in the reaction solution in the bottom, and the yields on the basis of NBD as the raw material were 42.4% and 6.2%, respectively. The above reaction was repeated to prepare 100 g (1.1 mol) of ECR. Meanwhile, in the repeated reaction, the total used amount of NBD was 191 g (2.7 mol).

Synthesis of di-TMP: A 3 L glass reaction vessel equipped with a reflux condenser, a thermometer, a dropping funnel and a stirrer was charged with 482 g (3.6 mol) of TMP and 1800 g of water, and these were mixed. Added dropwise into the flask were 100 g (1.1 mol) of the thus synthesized ECR, 200 g of a 40% formaldehyde aqueous solution (2.7 mol as formaldehyde) and 158 g of a 33% sodium hydroxide aqueous solution (1.3 mol as base) at room temperature over 30 min. After completion of the dropwise addition, the resultant was heated to 45° C. and further reacted for 210 min. As a result of subjecting the obtained reaction solution to GC, the amounts of TMP and di-TMP as calculated values were 401 g and 190 g, respectively, and the yields based on ECR were 19.5% and 67.1%, respectively.

Further, the cumulative yield of each of TMP and di-TMP based on NBD as the raw material from the synthesis of ECR were 14.4% and 28.5%, respectively, and a sum of the cumulative yields of TMP and di-TMP was 43.0%. In the case where TMP newly produced in the reaction was recycled in the subsequent reaction, the amount of TMP thus produced corresponds to 11% of an amount of TMP required in the subsequent reaction. The results are shown in Table 2.

TABLE 2

| | Raw materials (mol) | | Yield based on NBD (%) | | | produced TMP/TMP |
|---|---|---|---|---|---|---|
| | | | | | TMP + | as raw |
| | NBD | TMP | TMP | di-TMP | di-TMP | material |
| Example 1 | 1.9 | 0.81 | 57.5 | 28.1 | 85.6 | 1.34 |
| Example 2 | 1.9 | 0.81 | 59.0 | 24.9 | 83.9 | 1.11 |
| Example 3 | 1.9 | 1.0 | 65.5 | 22.0 | 87.5 | 1.01 |
| Comparative Example 2 | 2.7 | 3.6 | 14.4 | 28.5 | 43.0 | 0.11 |

INDUSTRIAL APPLICABILITY

The high-purity di-TMP is effectively used as a raw material for polyacrylates, polyether polyols, polyurethanes, alkyd resins, synthetic lubricating oils, etc. According to the method of the present invention, di-TMP is produced with a high efficiency.

The invention claimed is:

1. A method for producing ditrimethylolpropane by reacting n-butyl aldehyde ("NBD"), formaldehyde and a base, the method comprising the following steps:
   reacting the n-butyl aldehyde, a first formaldehyde and a first base to obtain a reaction mixture comprising trimethylolpropane ("TMP"), ditrimethylolpropane ("di-TMP") and 2-ethyl-2-propenal ("ECR");
   distilling the reaction mixture to recover the 2-ethyl-2-propenal therefrom; and
   sequentially or simultaneously adding to the reaction mixture from which the 2-ethyl-2-propenal has been recovered by the distillation the 2-ethyl-2-propenal recovered by the distillation and at least one of a second base or a second formaldehyde, and thereby proceeding the reaction gradually for production of the ditrimethylolpropane, and
   adding during any one or more of said reacting, distilling or sequentially or simultaneously adding step(s) a total amount of trimethylolpropane ranging from 0.1 to 2.0 equivalents per 1.0 mol of the n-butyl aldehyde;
   thereby producing ditrimethylolpropane.

2. The method according to claim 1, wherein a total amount of the trimethylolpropane added is from 0.3 to 1.0 equivalents per 1.0 mol of the n-butyl aldehyde.

3. The method according to claim 1, wherein a total amount of the first formaldehyde and the second formaldehyde is from 3.0 to 7.0 equivalents per 1.0 mol of the n-butyl aldehyde.

4. The method according to claim 1, wherein a total amount of the first base and the second base is from 0.8 to 2.5 equivalents per 1.0 mol of the n-butyl aldehyde.

5. The method according to claim 1, wherein an equivalent amount of the first base is from 5 to 100% of a total equivalent amount of the first base and the second base.

6. The method according to claim 1, wherein an equivalent amount of the first formaldehyde added in the reacting is from 9 to 100% of a total equivalent amount of the first formaldehyde and the second formaldehyde.

7. The method according to claim 1, wherein a temperature of a reaction in the reacting is from 45 to 120° C.

8. The method according to claim 1, wherein a temperature of the reaction mixture in the 2-ethyl-2-propenal is recovered by the distillation is from 45 to 120° C.

9. The method according to claim 1, wherein a temperature of a reaction in the adding is from 45 to 120° C.

10. The method according to claim 1, wherein in the adding, at least one of the formaldehyde and the trimethylolpropane is added simultaneously with addition of the 2-ethyl-2-propenal recovered by the distillation.

11. The method according to claim 10, wherein in the adding, the second formaldehyde is added simultaneously with addition of the 2-ethyl-2-propenal recovered by the distillation, and the addition of the second formaldehyde is terminated subsequently to termination of the addition of the 2-ethyl-2-propenal.

12. The method according to claim 1, wherein in the reacting, the trimethylolpropane is added before the reaction between the n-butyl aldehyde, the first formaldehyde and the first base.

13. The method according to claim 1, wherein a time required for the addition of the 2-ethyl-2-propenal recovered by the distillation is from 10 to 300 min.

14. The method according to claim 1, comprising adding TMP to the first reacting step.

15. The method according to claim 1, comprising adding TMP to the second distilling step.

16. The method according to claim 1, comprising adding TMP to the third sequentially or simultaneously adding step.

17. The method according to claim 1, further comprising isolating the di-TMP produced and, optionally, purifying it by distillation and/or crystallization.

18. The method according to claim 1, further comprising producing a polyacrylate, polyether polyol, polyurethane, alkyd resin, or synthetic lubricating oil from the di-TMP.

* * * * *